United States Patent [19]

Castellini

[11] Patent Number: 4,894,010
[45] Date of Patent: Jan. 16, 1990

[54] APPARATUS PREVENTING THE RETURN OF ATOMIZED SPRAY INTO DENTAL SURGERY INSTRUMENTS HAVING SEPARATE AIR AND WATER LINES

[75] Inventor: Franco Castellini, Bologna, Italy

[73] Assignee: Castellini S.p.A., Bologna, Italy

[21] Appl. No.: 193,883

[22] Filed: May 13, 1988

[30] Foreign Application Priority Data

May 29, 1987 [IT] Italy ................... 3497 A/87

[51] Int. Cl.⁴ ............................ A61C 1/00; A61C 3/00
[52] U.S. Cl. ................................. 433/27; 433/101
[58] Field of Search ................ 433/27, 28, 101

[56] References Cited

U.S. PATENT DOCUMENTS 3,718,974  3/1973  Buchtel et al. ................ 433/27

FOREIGN PATENT DOCUMENTS 0042267  5/1985  European Pat. Off. .
1166665  10/1969  United Kingdom .

Primary Examiner—Robert Peshock
Attorney, Agent, or Firm—Laff, Whitesel, Conte & Saret

[57] ABSTRACT

The apparatus prevents atomized fluid from being drawn back into the spray circuits of dental surgery instruments with separate air and water lines by virtue of incorporating a reservoir, installed on the air line at a point downstream of the relative control valve, the capacity of which is such as to ensure that air will continue to emerge from the instrument for a short duration after the control valve has closed.

8 Claims, 1 Drawing Sheet

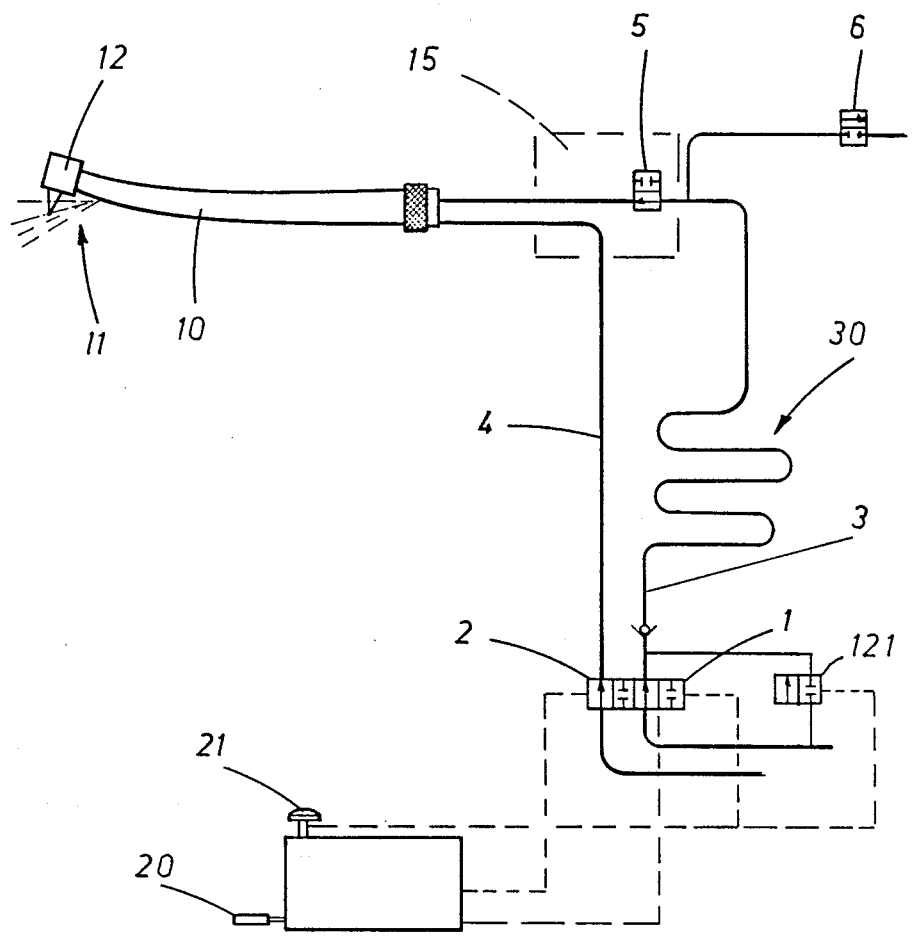

APPARATUS PREVENTING THE RETURN OF ATOMIZED SPRAY INTO DENTAL SURGERY INSTRUMENTS HAVING SEPARATE AIR AND WATER LINES

BACKGROUND OF THE INVENTION

The invention relates to apparatus the purpose of which is to prevent the return of atomized water into dental surgery instruments of the type having separate lines for air and water.

Given the ease with which infection is transmitted, especially via the bloodstream, it is of paramount importance that surgical instruments of all kinds be sterilized to avoid the spread of disease. This requirement is particularly important in the field of dentistry; numerous patients are treated each day, and it is well known that the oral cavity affords one of the easiest paths for the spread of infection.

Numerous devices or apparatus exist currently for the sterilization of single instruments (probes, implements etc.) that are brought into direct contact either with the teeth or with infectious media.

Sterilization is more problematic, however, in the case of power driven dental instruments, or rather of permanent systems and their associated parts, especially high speed drills and similar equipment, inasmuch as these are provided with two separate fluid lines for the supply of water and air; each such line is controlled by shut-off means, located remote from the instrument in most cases.

Operating the shut-off control, the dentist can cause the flow of air and water to cease without difficulty: whilst this presents no problem where the air is concerned, the outlet of the other line continues to drip water which, with the implement still in the oral cavity or suspended in mid-air nearby, constitutes a source of annoyance for the patient. Accordingly, means are adopted, installed at a given point along the water supply line, that will generate a marginally negative pressure on activation of the shut-off means and thus draw the water back into the line, preventing the formation of a drip.

Such a remedy creates drawbacks from the hygiene standpoint however; by generating suction in order to eliminate drips, it happens that spray previously atomized and still lingering (doubtless infected) in the oral cavity, is similarly drawn back through the instrument and into the water line.

The drawback in question can be counteracted with a conventional device by means of which it is possible to disinfect an instrument, or rather, the spray circuit of the system, following each session of treatment; this is effected by filling the spray circuit with a liquid disinfectant that is left to stand for a given duration, according to whether a swift cleansing operation or full sterilization is required, before being flushed out with a rinsing liquid.

Whilst such a method is valid enough in terms of end results, a certain amount of time is required between one patient and the next, in order to effect the disinfection/sterilization procedure.

The majority of equipment pedestals installed in modern dental surgeries incorporate an additional 'chip-air' facility, generally associated with the drill control pedal, which causes air only to emerge from the handgrip of the drill at a point adjacent to the cutting bit; the chip-air control by-passes the main solenoid operated shut-off valve governing the supply of air to the turbine, so that a burst of air can be produced at random (the drill being idle) and for the duration required, in order to clear the treatment area before and after drilling, without the need to discard the drill and take up a separate air instrument. Such an arrangement is disclosed, for instance, in GB No. 1166665.

In another system, disclosed in EP No. 042267, the chip-air control is connected to the drill foot pedal via a timer circuit, in such a way that when the pedal is released, closing the main solenoid operated air and water control valves, the chip control will cut in automatically and produce a burst of air from the handgrip for a set time lapse, of duration (2 ... 3 seconds) sufficient to clear the treatment area.

The object of the invention is one of overcoming hygiene problems that arise when suction is generated in the manner aforementioned, whilst avoiding the adoption of additional media, hence avoiding any extra lapse of time that might be dictated by their use.

SUMMARY OF THE INVENTION

The stated object is achieved with an apparatus as described and claimed herein, by means of which a flow of air is maintained from the relative outlet of the grip, following release of the foot pedal on terminating a drilling operation, without utilizing auxiliary valves to by-pass either the main control or the chip-air control media.

One of the advantages of the invention disclosed is essentially that of its simplicity and economy, in terms of construction.

Another advantage of the invention is the safety guaranteed from the hygiene standpoint.

BRIEF DESCRIPTION OF THE DRAWINGS

A preferred embodiment of the invention will now be described in detail, by way of example, with the aid of the one accompanying drawing, which is a diagram of the fluid lines and control components utilized in apparatus as disclosed.

DESCRIPTION OF THE PREFERRED EMBODIMENTS

In the drawing, 10 denotes the handgrip of a dental surgery instrument, in particular, of a high speed turbine drill, the front end of which carries a bit denoted 12; the instrument is connected up to two independent fluid lines 3 and 4, supplying air and water respectively.

The two fluid lines extend on through the grip 10 itself and emerge substantially at its tip, there combining to produce an atomized spray 11 that is played onto the bit 12 and also serves to clear and cool the treatment area.

1 and 2 denote first shut-off means installed on the two fluid lines 3 and 4, which serve to permit and prevent the supply of air and water to the grip 10. Such means 1 and 2 are embodied conventionally as electrically operated control valves, designed to open simultaneously when a pedal 20 is depressed by the operator: to activate the drill, the operator pushes down on the pedal, whereupon the two valves 1 and 2 open together and air and water can flow to the grip 10; releasing the pedal, flow is cut off. 21 denotes the 'chip-air' facility, an additional control by means of which the operator can activate the air line 3 to the grip, independently, and thus invest the drill bit 12 with a dry jet.

As the drawing illustrates, the chip-air control button 21 is connected in parallel with the pedal 20, and can open up the air line 3, independently of the pedal and for any given duration, either by operation of a solenoid operated by-pass valve denoted 121, or by direct action on the main air control valve 1.

Apparatus according to the invention comprises an air reservoir 30 installed on the relative supply line 3 at a point downstream of the main control and chip-air valves 1 and 121; in the example shown in the drawing, the reservoir is created by increasing the length of the supply line 3, though a similar effect might be produced by widening the bore, or indeed by installing a separate tank.

5 denotes second shut-off means located upstream of the grip 10, which are embodied as an on/off valve located on the air line 3 and incorporated into the table 15 that carries the grip 10 when not in use, so as to cut off the flow of air whenever the grip is replaced in its holder.

Finally, 6 denotes third shut-off means capable of exhausting pressure from the air line 3; such means might be embodied either as a normally closed valve interlocked to the on/off valve 5, or as a suitably calibrated restriction.

Operation of the apparatus disclosed will now be described.

In taking up the grip 10 and removing it from the table 15, the operator causes the on/off valve 5 to open and enable the drill for operation.

The instrument poised, the operator depresses the pedal 20 to open up the two main valves 1 and 2 and connect the grip 10 with the sources of fluid, whereupon air and water flow through the respective lines 3 and 4 and mingle to produce the atomized spray 11. Clearly, if the pedal 20 is released, the two valves 1 and 2 will close; however, while water will cease to flow through the relative line 4, air accumulated in the reservoir 30 will continue to flow to the grip and emerge from the holes at the tip, near the drill bit 12, for a duration that is dependent upon the capacity of the reservoir itself. The continued expulsion of air substantially creates a barrier, ensuring that atomized spray lingering in the oral cavity cannot be drawn back into the water circuit; at all events, the fact that the air and spray outlets face in the same direction will ensure that the spray outlet draws in only such fluid as is in close proximity to it—i.e. unadulterated air continuing to flow from the relative supply line 3.

Accordingly, a barrier is set up that can ensure hygienic conditions through the spray circuit as a whole.

Should the operator need to use the chip-air facility at any time during treatment to produce a jet of air, it will suffice to depress the control button 21, whereupon the relative valve 121 (or 1) opens up the line 3 and directs air through the grip 10 in the manner already described.

The valve denoted 6 comes into play in the event that the operator has to replace the instrument in its holder at the table 15 with a certain amount of air still occupying the reservoir 30, i.e. where the accumulated air has not been allowed to escape fully from the main air line 3 by way of the grip. Should air remain trapped under pressure in the line 3 when the on/off valve 5 closes, there will be an exhaust from the tip of the instrument when taken up again for use, whether the operator requires it or not. To avoid such an occurrence, it suffices either to interlock the opening movement of a normally closed type valve 6 to the closing movement of the on/off valve 5, or alternatively, to utilize a permanently open valve 6 with a calibrated orifice that will vent any residual pressure from the air line in a relatively short time whenever the on/off valve 5 closes.

What is claimed:

1. Apparatus to prevent the return of atomized spray into power driven dental surgery handpieces connected to separate air and water supply lines, comprising: shut-off air and water valve means connected to the air and water lines respectively and located between the air and the water lines and said dental handpiece;
    a dentist controller pedal connected to said air and water valves means to simultaneously open and close said air and water valve means;
    a compressed air reservoir connected in series with the air line at a point downstream of said air valve means, since compressed air reservoir having a capacity which is such that air will continue to flow from the handpieces for a short duration after closing said shut-off air and water valve means.

2. The apparatus of claim 1, wherein said air reservoir is also said air supply line.

3. The apparatus of claim 2, wherein the reservoir is realized by widening a bore of the air supply line.

4. The apparatus of claim 3, wherein the reservoir is realized by also increasing length of the air supply line.

5. The apparatus of claim 1, comprising an additional "chip-air" control device associated with said dentist controller pedal to supply a burst of air through the air supply line when said controller pedal is not operating and said "chip-air" control device connected directly to said shut-off air valve means in parallel connection with said controller pedal in order to close and open the air valve means.

6. The apparatus of claim 1, comprising an additional "chip-air" control device associated with said dentist controller pedal to supply a burst of air through the air supply line when said controller pedal is not operating and said "chip-air" control device connected to an independent shut-off air valve means located between the air line and said dental handpiece upstream of the reservoir.

7. The apparatus of claim 1, wherein the air supply line has a second shut-off valve means located on an instruments holding table and a third shut-off valve means located between said shut-off valve means and said second shut-off valve means, said third shut-off valve means being open when said second shut-off valve means closes the air line.

8. The apparatus of claim 1, wherein the air supply line has a second shut-off valve means located on an instruments holding table and a third calibrated valve means located between said shut-off valve means and said second shut-off valve means and said third calibrated valve means being open when said second shut-off valve means closes the air line in order to vent residual pressure from the air line.

* * * * *